United States Patent [19]

Sitnam

[11] Patent Number: 5,185,009
[45] Date of Patent: Feb. 9, 1993

[54] BIODEGRADABLE DIAPER

[76] Inventor: Elmo Sitnam, 1465 Charlotte Street, North Vancouver, British Columbia, Canada, V7J 1H1

[21] Appl. No.: 782,739

[22] Filed: Oct. 28, 1991

Related U.S. Application Data

[63] Continuation of Ser. No. 377,350, Jul. 10, 1989, abandoned.

[51] Int. Cl.$^5$ .................. A61F 13/15; A61F 13/20
[52] U.S. Cl. ........................... 604/364; 604/358; 604/367; 604/385.1; 604/385.2
[58] Field of Search ............ 604/365, 367, 369, 374, 604/375, 378, 385.2, 389, 391, 383, 358, 364, 385.1

[56] References Cited

U.S. PATENT DOCUMENTS

| | | | |
|---|---|---|---|
| 3,595,235 | 7/1971 | Jespersen | 604/364 |
| 3,630,201 | 12/1971 | Endres | 604/378 |
| 3,658,062 | 4/1972 | Kapur | 604/378 |
| 3,665,923 | 5/1972 | Champaigne, Jr. | 604/364 |
| 3,881,487 | 5/1975 | Schrading | 604/364 |
| 3,902,493 | 9/1975 | Baier et al. | 604/286 |
| 3,952,347 | 4/1976 | Comerford et al. | 604/368 |
| 4,069,177 | 1/1978 | Smith | 47/DIG. 10 |
| 4,282,874 | 8/1981 | Meser | 604/365 |
| 4,323,874 | 4/1982 | Jones et al. | 525/54.32 |
| 4,515,595 | 5/1985 | Kievit et al. | 64/385.2 |
| 4,755,550 | 7/1988 | Shuman et al. | 524/270 |
| 4,769,414 | 9/1988 | Kightlinger et al. | 525/54.24 |
| 4,834,738 | 5/1989 | Kielpikowski et al. | 604/358 |
| 4,944,734 | 7/1990 | Wallach | 604/358 |
| 4,964,857 | 10/1990 | Osborn | 604/397 |
| 5,009,648 | 4/1991 | Aronoff et al. | 604/332 |
| 5,019,069 | 5/1991 | Klemp | 604/387 |

FOREIGN PATENT DOCUMENTS 3338201  4/1984  France .................. 604/389

OTHER PUBLICATIONS

The Condensed Chemical Dictionary, Tenth Edition, Gessner G. Hawley p. 130.

*Primary Examiner*—Randall L. Green
*Assistant Examiner*—Zuttarelli A.
*Attorney, Agent, or Firm*—Shlesinger, Arkwright & Garvey

[57] ABSTRACT

A biodegradable diaper. The diaper has an outer sheet of biodegradable material able to resist water absorption. An inner sheet of biodegradable material is able to allow the passage of water and is attached to the outer sheet by a biodegradable adhesive at the periphery to form an envelope. A super absorbent core is located within the envelope. There is a water resistant film of biodegradable material located within the core to assist in fluid distribution into the core.

13 Claims, 1 Drawing Sheet

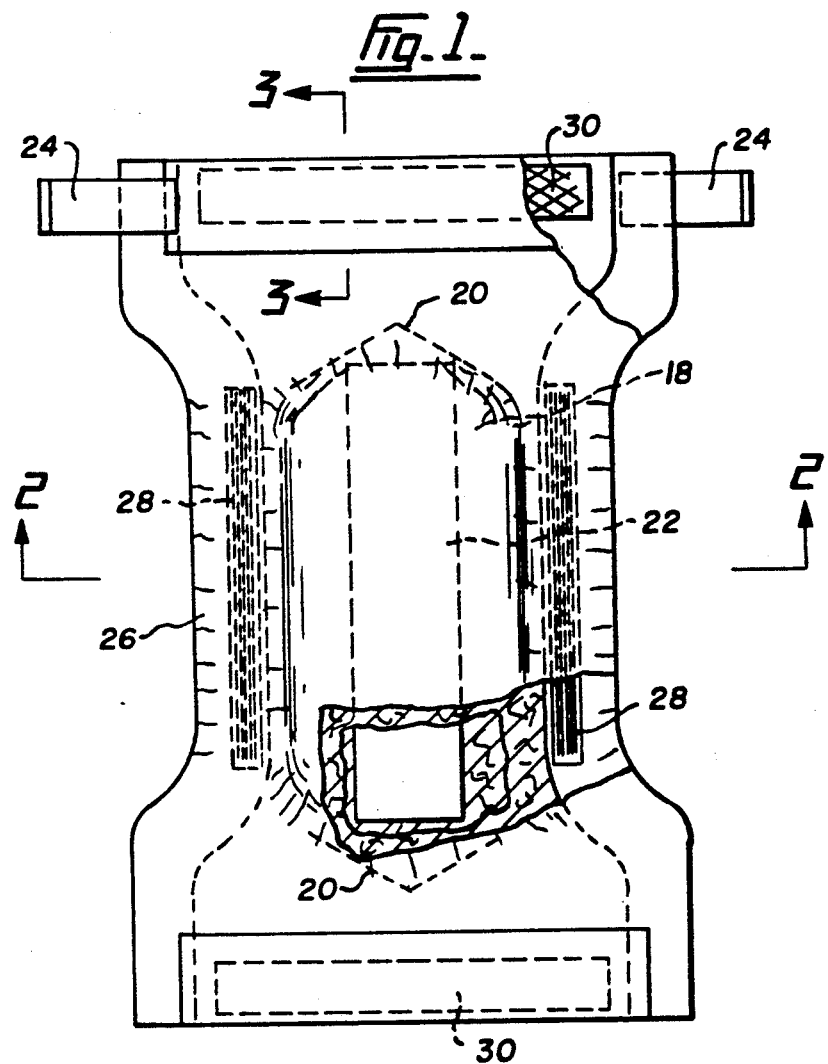
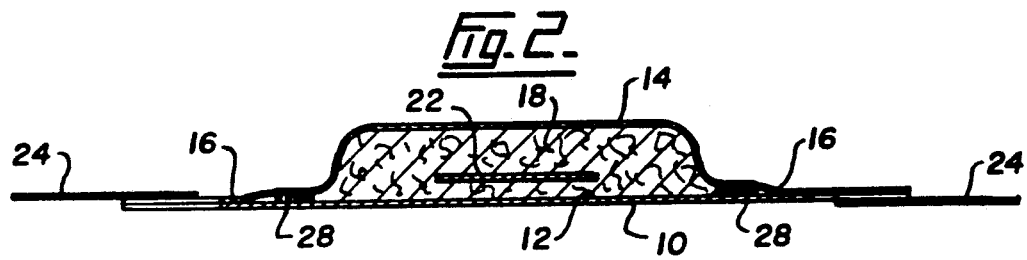
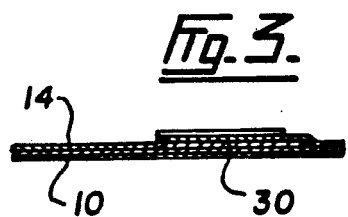

BIODEGRADABLE DIAPER

This application is a continuation, of application Ser. No. 07/377,350, filed Jul. 10, 1989 now abandoned.

FIELD OF THE INVENTION

This invention relates to a biodegradable diaper.

DESCRIPTION OF THE PRIOR ART

For many years diapers were used over and over again, being washed between each use. With the advent of families in which both the husband and the wife work there was a great interest in reducing tedious household chores, for example the washing of diapers. This introduced a massive demand for the disposable diaper, generally speaking a cheaply made diaper that, as the name implies, can be used once and then discarded. The tedium of laundering the traditional cotton diaper is thus avoided.

Disposable diapers have been so popular that they now present a pollution problem. There is considerable concern that these diapers, when placed in domestic garbage and, for example, disposed of in landfill, represent an environmental hazard. In addition to the obvious problems of human waste the materials used in the diapers are durable and become part of the environment. As these materials are plastics they are not a welcome part of the environment and cannot be removed by natural means. Accordingly, there is a keen interest in avoiding these environmental hazards which, so far, have involved encouraging young families to revert to washable, cotton diapers.

Although this is environmentally sound, nevertheless it avoids the question that originally prompted the use of disposable diapers, namely ease of use and avoidance of household chores.

It is believed that a preferred course of action, combining the virtues of disposable diapers and avoidance of environmental hazard, is the use of biodegradable diapers. Biodegradable is a term indicating that the materials used can be degraded in the environment, typically because of ultraviolet light destroying the polymeric structure or by the fact that the materials deteriorate, for example in the presence of water.

There have been no biodegradable diapers produced so far.

SUMMARY OF THE INVENTION

The present invention accordingly seeks to produce a diaper that is wholly biodegradable.

Accordingly the present invention is a biodegradable diaper comprising an outer sheet of biodegradable material able to resist water absorption; an inner sheet of biodegradable material able to allow the passage of water and attached to the outer sheet by a biodegradable adhesive at the periphery to form an envelope; a super absorbent core within the envelope; and a water resistant film of biodegradable material located within the core to assist in fluid distribution into the core.

In a preferred embodiment the outer sheet is of rayon, for example of polypropylene. The inner sheet is of polyethylene. A biodegradable adhesive that has proved useful in the formation of the envelope is a natural rubber latex.

The essence of the present invention may be considered to be the biodegradable, super-absorbent core. In one aspect this core may be a sulfite cooked pulp subjected to a hammer mill. Hemlock is an appropriate wood for production of the pulp.

In a further embodiment the super absorbent core may be made of starch grafted polyacrylonitrile copolymer. Preferably the copolymer is saponified.

In this process starch is grafted with acrylonitrile chains, typically using a cerium catalyst, usually ceric ammonium nitrate. In a particularly desirable aspect the graft copolymers are saponified in conventional manner using aqueous bases, typically sodium hydroxide.

The film within the core may, for example, be a film of biodegradable polyethylene.

The diaper desirably includes fastening tabs at 2 of the 4 corners. These tabs, which must, of course, be biodegradable, are desirably made of cellulose.

In accordance with what is now standard diaper practice it is desirable to incorporate elastication at the sides to ensure that the diaper is a snug fit at the crotch of the infant. This may be achieved by arranging elongated rubber strips at the sides of the diaper. Natural rubber is a biodegradable material.

It is particularly desirable to incorporate resilient, biodegradable waist strips at each end of the diaper, as these greatly facilitate the fit of the diaper.

The biodegradable waist strips may be polyurethane polyester foams.

DESCRIPTION OF THE DRAWINGS

The invention is illustrated, merely by way of example, in the drawings in which:

FIG. 1 is a plan view of a diaper according to the present invention;

FIG. 2 is a section on the line 2—2 of FIG. 1; and

FIG. 3 is a section on the line 3—3 of FIG. 1.

DESCRIPTION OF THE PREFERRED EMBODIMENTS

The drawings show a diaper comprising an outer sheet 10 of biodegradable material able to resist water absorption.

There is an inner sheet 14 of biodegradable material that is attached to the outer sheet 10 by a biodegradable adhesive 16 at the periphery to form an envelope—see FIG. 2.

A super-absorbent core 18 is located within the envelope. If necessary, adhesive 20 may be applied to the super-absorbent core 18 to ensure that it is retained in position in the envelope.

A water resistant film 22 of biodegradable material is located within the core 18 to assist fluid distribution into the core.

The illustrated embodiment includes fastening tabs 24 at two of the four corners. These tabs typically have an adhesive applied to them and protective sheets for the adhesive. The tabs can be adhered to the other end of the diaper to secure the diaper in position on an infant. The tabs 24 may be a combination of paper and cellulose film, which is biodegradable.

In accordance with standard practice in the disposable diaper art, the diaper has a narrow section 26 that fits between the legs of the infant. In this section it is desirable to include elastication to ensure a snug fit and, in particular, avoidance of leakage. Natural rubber strips 28 are therefore incorporated and located by the gluing together of the films. The natural rubber may be mixed with other ingredients to improve its biodegradability.

There are resilient, biodegradable waist strips 30 at each end of the diaper. These strips may, for example, be a polyurethane polyester foam and act again to improve the fit of the diaper on the infant. The arrangement is shown particularly in FIG. 3.

In an embodiment of the invention that has proved useful the outer sheet 10 was a biodegradable polypropylene film that available under the trade mark MSDS from Clopay Corporation of Ohio. The inner sheet 14 of biodegradable material was biodegradable polyethylene available from the plastic products division of Clopay Corporation of Ohio.

The super-absorbent core 18 was, in one embodiment, prepared from a fluff pulp available under the trade mark Rayfloc-P from ITT Rayonier Inc. in Connecticut. This is a sulfite cooked hemlock pulp supplied in either rolls or sheets for fluffing. It is fluffed by a hammer mill, and produces a fluff having excellent absorbent properties.

In a further embodiment, the super-absorbent core 18 was made from the material available under the trade mark Water Lock D-212 and D-223, available from Grain Processing Corporation in Iowa. These compounds are chemically classified as the solution and aluminum salts of starch-graft (poly-Z propenamide-co-Z-propenoic acid).

Alternatively, saponified starch-graft polyacrylo nitrile copolymers have been used. These are starch acrylo nitrile grafts initiated using ceric ammonium nitrate. They were invented by the USDA in the 1960's, particularly by Gugliemelli, Weaver and Russell of the USDA.

The adhesive 20 and, indeed, the adhesive used in all places in the disposable, biodegradable diaper of the invention, was a natural rubber latex available from ITT Rayonier Inc. of Connecticut under their trade description 34-2881. The material is a hot-melt adhesive.

The water resistant film 22 located within the superabsorbent core 18 was the same polyethylene used for inner sheet 14.

The fastening tabs 24 were a combined paper and cellulose film available under the trade designation XC-0106. These are paper backed cellulose.

The waist strips 30 are available from Caligen in the United Kingdom and are a polyester polyurethane foam. The polyester resin is a condensation product of adipic acid, diethylene glycol and pentaerythritol. The polyester was copolymerized with toluene diisocyanate. Amine catalysts were included and the mix also included silicone surfactant and water. Plasticizers were used as necessary.

I claim:

1. A biodegradable diaper comprising:
   a) an outer sheet having a periphery of biodegradable material able to resist water absorption;
   b) an inner sheet of biodegradable material able to allow passage of water therethrough and attached to the periphery of said outer sheet by a biodegradable adhesive to form an envelope having walls and defining a space therein;
   c) said envelope having a waist portion and leg portions formed therein;
   d) a biodegradable super absorbent core disposed within said envelope comprising a uniform material and substantially occupying all of said space within said envelope;
   e) a water resistant film of biodegradable material having a peripheral edge surface, said film positioned within said core for assisting in fluid distribution into said core, said film edge surface substantially spaced from said envelope walls and extending substantially parallel to said inner and outer sheet of said envelope; and
   f) strips of resilient biodegradable polyurethane polyester foam attached at said waist portion to allow said diaper to gather about a user's waist.

2. A diaper as claimed in claim 1 in which said outer sheet is of rayon.

3. A diaper as claimed in claim 1 in which said outer sheet is polypropylene film.

4. A diaper as claimed in claim 1 in which said inner sheet is of polyethylene.

5. A diaper as claimed in claim 1 in which said biodegradable adhesive is rubber latex.

6. A diaper as claimed in claim 1 in which said super absorbent core is of wood fluff.

7. A diaper as claimed in claim 6 in which said wood fluff is sulfite cooked hemlock pulp.

8. A diaper as claimed in claim 1 in which said super absorbent core is starch graft polyacrylonitrile copolymer.

9. A diaper as claimed in claim 8 in which said copolymer is saponified.

10. A diaper as claimed in claim 1 in which said film within said core is polyethylene.

11. A biodegradable diaper as recited in claim 1, and further comprising:
    a) said outer sheet provided with fastening tape for securing said diaper about the user.

12. A biodegradable diaper as recited in claim 11, and wherein:
    a) said fastening tape comprising a cellulose film having an adhesive coated thereon.

13. A biodegradable diaper as recited in claim 1, and further comprising:
    a) strips of natural biodegradable rubber attached between said inner sheet and said outer sheet at said leg portions to allow said diaper to gather about the users crotch.

* * * * *